United States Patent [19]

Bennett et al.

[11] Patent Number: 4,721,735

[45] Date of Patent: Jan. 26, 1988

[54] FRANGIBLE LIGHT CURED COMPOSITIONS

[75] Inventors: Richard J. Bennett, Milford; Robert V. Hare, Georgetown, both of Del.

[73] Assignee: Dentsply Research and Development Corporation, Milford, Del.

[21] Appl. No.: 821,774

[22] Filed: Jan. 23, 1986

[51] Int. Cl.$^4$ .............................. C08J 6/10; A61K 6/08; C08F 20/54; C08L 39/00

[52] U.S. Cl. ....................................... 522/71; 523/109; 523/115; 523/116; 523/117; 523/120; 524/555; 526/301

[58] Field of Search ................... 522/71; 523/109, 120, 523/115, 116, 117; 526/301; 524/555

[56] References Cited

U.S. PATENT DOCUMENTS

| | | | |
|---|---|---|---|
| 3,503,128 | 3/1970 | Boyd | 523/116 |
| 3,709,866 | 1/1973 | Waller | 523/115 |
| 4,089,763 | 5/1978 | Dart | 523/115 |
| 4,372,836 | 2/1983 | Schmitt et al. | 522/71 |
| 4,394,494 | 7/1983 | Miyake | 526/301 |
| 4,399,239 | 8/1983 | Herwig et al. | 522/71 |
| 4,404,296 | 9/1983 | Schapel | 523/109 |
| 4,440,878 | 4/1984 | Kawahara | 523/116 |
| 4,457,818 | 7/1984 | Denyer | 526/301 |
| 4,469,477 | 9/1984 | Potter | 523/120 |
| 4,491,453 | 1/1985 | Koblitz | 523/116 |
| 4,530,992 | 7/1985 | Jones | 523/109 |

*Primary Examiner*—Joseph L. Schofer
*Assistant Examiner*—Peter D. Mulcahy
*Attorney, Agent, or Firm*—Woodcock Washburn Kurtz Mackiewicz & Norris

[57] ABSTRACT

Novel compositions, especially light curable compositions, are provided which are coherent, but frangible when cured. Preferred compositions comprising a major proportion of inert, preferably inorganic filler material, polymerizable resin and frangibility enhancing material are provided which are light curable. The materials are particularly useful for "temporary" dental fillings and removable endodontic fillings. The cured materials are easily dissected, comminuted and removed as desired after curing without trauma to the filled teeth.

27 Claims, No Drawings

FRANGIBLE LIGHT CURED COMPOSITIONS

BACKGROUND OF THE INVENTION

This invention is concerned with actinic light curable compositions which, when cured, are frangible. By this is meant that such cured compositions retain their coherency, physical integrity, and shape, resist disintegration and retain their original, general properties, they are capable of being easily cut, comminuted, dissected, excavated, or otherwise caused to lose their physical shape and integrity when desired. This invention deals with materials which are suited to applications where a form or cavity is filled on a temporary basis to seal it against the ingress of water, fluids, bacteria and the like. Such materials are particularly useful in dental, endodontic, and other medical, dental and industrial applications where it is desired to provide a reasonably hard, easily formed, and quickly hardenable shaped mass of material which can be removed from a dental space after curing without excessive difficulty or substantial trauma. Exemplary of these uses are "temporary fillings" for dental cavities and removable endodontic fillings.

Materials which are suitable for the temporary restoration of excavated carious lesions, voids or other cavities in teeth have been known heretofore. Such restorations, colloquially known as "temporary fillings", are indicated in many situations where permanent filling or restoration of a tooth is not called for. Materials useful for such purposes must be capable of firmly filling a prepared tooth space, such as an excavated cavity, without substantial leakage and with reasonable hardness while at the same time being capable of being removed as necessary either in whole or in part without substantial additional trauma to the tooth involved.

In endodontics, it is frequently necessary to provide repeated access to the pulpal space of a diseased, dead or dying tooth. In this regard, the pulpal space of such a tooth is excavated by the endodontic practitioner using a conventional array of tools. The diseased portions of the tooth are removed and the spaces cleaned of debris and detritus. Typically, the space is then medicated in order to suppress any remaining infection, to soothe the traumatized tissue, or otherwise to improve the endodontic environment. For this purpose, medicated paper "points", treated cotton pledgets or other forms of medicament are conventionally inserted into the excavated endodontic space, left for a period of time, usually a few days, and then removed. Such treatment may be repeated several times during the course of the endodontic protocol. It is obviously necessary to seal the pulpal space from the oral environment during these periods of medication or other treatment. For this purpose, the pulpal space is, ideally, filled towards its external portion with a material which is sufficiently strong and coherent to isolate the space from the oral environment, but which can, subsequently, be removed without substantial additional trauma being inflicted upon the tooth.

Dental spaces have been temporarily sealed heretofore by formulations of zinc oxide and eugenol. One such material is IRM$^R$, a trademark of the L.D. Caulk division of Dentsply International Inc., assignee of this invention. IRM$^R$ is a polymer reinforced zinc oxide-eugenol which requires considerable time to harden. While adequate, such simple mixtures of zinc oxide and eugenol have not shown exceptional utility for this purpose since they are not particularly strong, are difficult to mix and manipulate, and tend to leak about the cavity margin.

Traditional dental restorative compositions have also been used heretofore in these roles. Their removal, however, is generally difficult, since these materials have been formulated to exhibit great strengths and to resist removal from a cavity and disintegrative forces. One such traditional restorative is PRISMA FIL$^R$, a product of the L. D. Caulk division of Dentsply International Inc., assignee of the present invention. PRISMA FIL$^R$ is a visible light curable dental restorative generally described in U.S. Pat. No. 4,491,453—Koblitz et. al. Other restorative compositions, including other actinic light curable restorative compositions, have been known heretofore.

Another presently available material, CAVIT (a trademark of the Espe Company), has been offered for temporary endodontic sealing. This material, which is believed to comprise a polyvinyl acetate-based formulation believed to contain calcium sulfate hemihydrate, is water sorptive and has a tendency to leak fluids into the pulpal space—a decidedly undesirable effect. This material hardens very slowly requiring uptake of moisture.

It is greatly desired to provide materials which are coherent and reasonably strong, which harden upon command and which do not leak, but which are capable of being removed easily when desired.

See in this regard "The Leakage of Materials Used As Endodontic Dressing Seals", TYDSKRIF Van Die T.V.S.A.—Valcke et al June 1978, incorporated herein by reference.

OBJECTS OF THE INVENTION

It is a principal object of this invention to provide compositions which are frangible after curing.

It is another object to provide frangible materials which can be easily removed in whole or in part from a dental space.

It is a further object to provide such compositions which are actinic, especially visible, light curable.

A further object is to provide such compositions which are suitable for use in the temporary filling of dental cavities and the like.

A further object is to provide such compositions which are adapted for the removable filling of at least a portion of an endodontic space.

The provision of actinic light curable, especially visible light curable, compositions which can be cured into coherent, reasonably hard and durable materials, but which are capable of being easily comminuted, or removed by conventional hand or rotary cutting instruments when desired is a further object of this invention.

Yet another object is to provide methods for treating teeth in a reversible fashion.

A still further object is to provide coherent, but frangible, shaped bodies.

Yet another object is to provide pre-mixed, one component compositions which are chemically compatible with the oral environment.

Other objects will be apparent to those of ordinary skill in the art from a consideration of the present specification.

SUMMARY OF THE INVENTION

A new class of compositions which is especially suited for use in dentistry and endodontics has been discovered which possesses a spectrum of properties not known heretofore. Compositions have been discovered which are rapidly curable by irradiation with actinic light into shaped bodies or other masses which are, at once, coherent in form and possessed of physical integrity, shape, and physical properties normally desirable for endodontic applications. Surprisingly, such are rendered suitable for dental and endodontic use while at the same time being frangible. Thus, the cured, shaped bodies or masses can be comminuted using hand tools or low-torque mechanical equipment. These materials, the cured, shaped bodies shaped therefrom, and the related processes for employing them, are a distinct departure from prior developments.

The present materials are amenable to pre-mixing and one component dispensing. The materials of this invention are distinct from prior actinic light curable compositions which have uniformly been directed towards ever increasing hardness, durability, and overall strength so as to render them increasingly useful for permanent dental restorative work. One of ordinary skill in the dental arts would be suprised indeed at the suggestion that a visible light curable dental composition should be formulated so as to be relatively weak rather than as strong as possible.

At the same time, the compositions of this invention are a departure from prior "temporary" filling materials known to the dental arts. There has been a long-felt need for improved "temporary" filling materials, especially in view of the tendency of presently available materials to leak around the marginal walls of prepared tooth spaces which they occlude. Thus, the frangible, actinic light curable materials of the present invention are a distinct departure from the zinc oxide-eugenol and polyvinyl acetate compositions which are presently used.

In accordance with the invention, there are provided actinic light curable compositions which are frangible when cured. These comprise a major proportion of filler along with a minor proportion of polymerizable resin or resin blend along with frangibility enhancing material in an amount sufficient to render the cured composition frangible. A photosensitizing system is also included which is capable of curing the composition upon irradiation with actinic, preferably visible, light.

The polymerizable resin or resin blend comprises one or more ethylenically unsaturated materials, preferably oligomers, which are polymerizable upon irradiation with actinic light in the presence of a photosensitizing system. A wide variety of such materials are known to those of ordinary skill in the art and many are disclosed in U.S. Pat. No. 4,491,453—Koblitz et al., incorporated herein by reference.

The polymerizable resin preferably comprises a blend of two or more different types of polymerizable materials, urethane acrylic resin, and urethane polyether resin. The urethane acrylic and urethane polyether resins are preferably provided in complementary ratios of from about 15% to about 85% by weight of such a resin blend.

The present invention also provides methods of treating teeth, especially human teeth, comprising placing an actinic light curable composition into a prepared space in the tooth and irradiating the composition with actinic light for a time sufficient to cure the composition. The resulting, cured composition is a coherent mass, but one which is frangible. In accordance with a preferred embodiment, the actinic light is in the visible spectrum.

Methods of forming coherent, but frangible, shaped bodies are also provided which comprise forming an actinic light curable composition into a shape, and irradiating the shaped composition with actinic light for a time sufficient to cure it to provide the shaped body.

The compositions of this invention comprise inert fillers which may be any of a wide variety of filler materials conventionally used in light curable compositions which are compatible with the oral environment and generally unreactive toward the other components of the subject compositions. Those of ordinary skill in the art will appreciate that, for a given resin formulation, judicious choice of filler type and filler particle size must be made. The filler used must be such that the transmittance of actinic light through the restorative compositions is not impeded and is sufficient for polymerization to take place. At the same time, the selection of fillers must be such as to be consistent with the overall objectives of the present invention, that is, to provide curable materials which are capable of maintaining their physical structure upon curing, but which are also frangible when cured. As persons of ordinary skill in the art will recognize, the amount of filler and resin system will depend upon several variables including the identity of the resins and fillers and the particle sizes of the fillers.

A wide variety of filler materials are suited for use in the invention. These include inorganic glasses such as barium aluminum silicate, lithium aluminum silicate, strontium, lanthanum, tantalum, etc. glasses and related materials. Silica, quartz, borosilicates, aluminosilicates and many other fillers may also be employed. Metal oxides are also useful such as alumina, magnesia, baria etc. Organic fillers such as, for example, suspension or solution polymers of methyl methacrylate and its copolymers may also be advantageously employed. Mixtures of fillers are generally preferred. In accordance with a preferred practice of the present invention, barium boron aluminosilicate glass is used together with fused quartz, silanated aluminum oxide and hydroxylated silicon dioxide fillers. This blend has been found to be particularly well-suited to the practice of the invention.

Prior compositions have been designed to maximize strength, durability and integrity of the cured materials, i.e., not to be frangible. In such materials, it has been preferred to use smaller sizes of inorganic filler and to treat the filler particles with materials such as wellknown silanating agents to improve compositional strengths. While in the present invention particle sizes may vary, and while some of the filler particles which are used in the present invention may preferably be silanated, in general it is preferred to employ relatively large particles of inorganic filler (i.e. greater than about 5 microns on average) and to avoid silanation of the majority of the particles.

Preferred compositions comprise a major proportion of inert filler. It is preferred that the inert fillers used in the practice of the invention comprise from about 55% to about 85% of the composition by weight. It is more preferred that the fillers comprise from about 60% to about 80% of the composition and still more preferred that they comprise from about 65% to about 75% by weight of the composition.

The compositions of the present invention further comprise from about 15% to about 45% by weight of the composition of polymerizable resin or resin blend. It is more preferred that the composition comprise from about 20% to about 35% by weight and still more preferred that the composition comprise from about 20% to about 30% by weight of polymerizable resin blend. The resin or blend, itself, may comprise a wide variety of non-volatile ethylenically unsaturated oligomers such as acrylic-type oligomers known to the art such as, for example, bis GMA; (poly)ethylene acrylates and methacrylates, polyesters and other methacrylates, etc. However, in a preferred embodiment, the polymerizable resin blend comprises urethane acrylic resin, urethane polyether resin, and includes a photosensitizing system.

Urethane acrylic resins useful in the practice of the invention generally comprise the equimolar reaction products of hydroxylated acrylic esters and an aromatic or aliphatic mono- or preferably diisocyanate. The hydroxylated acrylic esters generally conform to the formula:

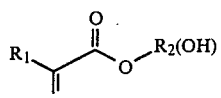

wherein $R_1$ is H or lower alkyl and $R_2$ is alkyl having from 1 to about 8 carbon atoms, or alkaryl with the alkyl portion having from about 1 to about 8 carbon atoms. Exemplary compositions of this family are the acrylic, methacrylic, ethacrylic etc. esters of hydroxymethyl, hydroxyethyl, hydroxypropyl etc. alcohols. Hydroxypropyl methacrylate has been found to be particularly preferred.

Other members of the class are illustrated by esters based on bisphenol-A and other aromatic nuclei. Thus, the acrylic and methacrylic adducts with bisphenol-A glycidate are useful; bis-GMA is preferred.

The hydroxylated acrylic esters are reacted with aliphatic or aromatic mono- or preferably diisocyanate in about 1:1 stoichiometry to yield the urethane acrylic resins useful in the invention. The preferred isocyanates are the alkyl and aryl diisocyanates having from about 3 to about 12 carbon atoms. Exemplary of these are hexamethylene, phenylene, 2,2,3-trimethylhexamethylene and other diisocyanates. Most preferred are the hexamethylene and 2,2,3-trimethylhexamethylene diisocyanates.

Preferred urethane acrylic resins are the reaction products of bis-GMA with hexamethylene diisocyanate and of hydroxypropyl methacrylate with 2,2,3-trimethylhexamethylene diisocyanate with the latter being most preferred. Many other compositions are useful, however. The urethane acrylic resins useful in the invention are generally familiar to practitioners in the art who are knowledgeable about their preparation. While one-to-one adducts are preferred, different ratios may find utility in some embodiments.

The urethane polyether resins most useful in the practice of the invention are those radiation polymerizable polyethers generally described in U.S. Pat. No. 4,233,425—Terfertiller et al., which is incorporated herein by reference. While it is believed that many of the members of the urethane polyether resin class may find utility in the practice of the invention, reaction products of polyalkylene polyols with isocyanate-modified acrylic esters are preferred. Thus, preferred resins may preferably include the isocyanatoalkyl-lower acrylic ester adducts with polyalkylene glycols. Exemplary, preferred materials are the isocyanatoethyl acrylate and methacrylate adducts with polyethylene, polypropylene-etc. glycols. The polypropylene glycol adduct with isocyanatoethyl methacrylate has been found to be most preferred.

Each of the urethane acrylic and the urethane polyether resins are preferably present in the polymerizable resin blend in proportions of from about 15% to about 85% by weight of the blend, i.e., proportions of about 1:6 to about 6:1. It is more preferred that the respective resins be present in the resin blend in weight proportions of about 1:5 to about 5:1 and still more preferred that they be present in ratios of from about 1:4 to about 4:1. It has been found that by varying the respective proportions of urethane acrylic resin and urethane polyether resin within the resin blend for use in the practice of the present invention, the resulting compositions are capable of yielding, after curing, shaped bodies or masses which have differing physical properties. More particularly, it is possible to alter the frangibility and other physical characteristics of the resulting, cured compositions by modifying the respective ratios of these resins. In general, an increase in the urethane acrylic resin component results in a less frangible, cured material, while an increase in the urethane polyether proportion results in increased frangibility of cured articles prepared from the compositions.

Those of ordinary skill in the art will appreciate that the frangibility of shaped bodies and cured masses formed from compositions in accordance with the present invention will also depend upon factors besides the ratio of the urethane acrylic and urethane polyether resins. Thus, the amount and identity of the inorganic filler materials, the respective proportions of inorganic filler to polymerizable resin blend, and the identity and amount of frangibility enhancing material such as particulate organic polymer will also affect the frangibility of the cured compositions.

The polymerizable resin blend further comprises a photosensitizing system capable of curing the composition upon irradiation with actinic light. Such photosensitizing systems are well known to persons skilled in the dental arts, albeit not in connection with the preparation of temporary filling materials or compositions capable of forming frangible, cured product. In general, such photosensitizing systems may be either designed to operate upon irradiation with ultraviolet light or visible light, or both.

Exemplary photosensitizing systems for use with ultravoilet light are described in U.S. Pat. No. 3,709,866—Waller, assigned to the assignee of this invention. This patent is incorporated herein by reference. Exemplary materials used for photosensitizing in this regard are benzoin methyl ethers. Ultraviolet curing systems have been used commercially in dental restorative products NUVA-FIL[R] and NUVA-FIL P.A.[R] which are registered trademarks for products past or present of the L. D. Caulk division of Dentsply International.

It is also known to provide compositions, including dental compositions, which are curable by action of visible light. Such photosensitizing systems are preferred for use in conjunction with the present invention. Exemplary visible light photosensitizing systems are described in U.S. Pat. No. 4,491,453—Koblitz et al, assigned to the assignee of the present invention. Additional systems are disclosed in U.S. Pat. No. 4,071,424—Dart et al. These patents are incorporated herein by reference.

The photosensitizing system preferably employed in the formulation of dental materials according to the practice of this invention is sensitive to visible light and comprises two components, an alpha diketone photosensitive species (also known as an alpha beta diketone) and an amine reducing agent. While any alpha diketone which is capable of initiating polymerization in the polymerizable systems of this invention is preferred, camphoroquinone, benzil, biacetyl, 9-10-phenanthrenequinone, and naphthoquinone are most preferred. Non-aromatic alpha diketones, especially camphoroquinone and biacetyl, have been found to be the most preferred photoinitiators for use in the practice of this invention. Camphoroquinone is presently most preferred.

The alpha diketone is combined with an amine reducing agent; the two taken together form the visible light sensitizing system useful for the practice of this embodiment of the invention. Numerous amines have been found to be useful as reducing agents for the alpha diketones used herein. Thus, aliphatic and aromatic amines such as tributylamine and tripropylamine are useful. Still more useful are substituted amines such as N-alkyl-dialkanolamines and trialkanolamines; especially N-methyldiethanolamine. Most preferred is ethyl 4-dimethylaminobenzoate. Those skilled in the art will appreciate that numerous other alpha diketones and amine reducing agents may be employed without deviating from the spirit of this invention, however.

The photosensitizing system is present in an amount effective to cause curing, i.e. substantial, preferably substantially complete polymerization, of the compositions of this invention upon irradiation with light of a suitable wavelength. For compositions designed to be visible light curable, photosensitizing compositions sensible to the visible spectrum are obviously preferred.

Numerous ultraviolet and visible light sources are known to those of ordinary skill in the art which may be effective to cure the compositions by causing substantial polymerization thereof. Preferred devices are the PRISMA LITE$^R$ and PRISMETICS-LITE TM visible light sources and NUVA LITE$^R$ ultraviolet light source available from Dentsply International, Inc.

The components of the photosensitizing system are, conventionally, provided in relatively small amounts, usually less than about 1% by weight of the compositions. In any event, they are present in an amount which is sufficient to cause substantial polymerization of the resulting compositions within an acceptably short period of time upon irradiation with a suitable source of actinic light. While it is convenient to refer to the photosensitizing system as being a part of the polymerizable resin blend, it will be appreciated that the photosensitizing system components are not, themselves, necessarily polymerizable. These materials may thus be incorporated in any convenient fashion within the compositions of the present invention.

Unlike previous light curable compositions for use in dentistry and otherwise, the present compositions are not designed to be as strong, rugged and durable as possible, but rather, to have sufficient strength to resist normal biting forces while possessing inherent weaknesses and retaining good sealing properties. One source of weakness has been described hereinabove in connection with the proportions of the components of the polymerizable resin blend. Additionally, selection of relatively large sized inorganic filler particles and the reduction of the common practice of extensive silanation of such fillers further contributes to frangibility in cured compositions of the invention.

A principal source of frangibility in the cured compositions, however, is the inclusion of frangibility enhancing agents. These materials are preferably particulate polymers, especially suspension and solution polymers, which have relatively low tensile strenghts. Those of ordinary skill in the polymer arts will appreciate that a number of such polymers exist including polyethylene, polypropylene, polybutylene, and other polyalkylenes along with a host of other materials. Copolymers and mixtures of polymers are, similarly, useful for this purpose.

These frangibility enhancing materials are best described by what they do rather than by what they are. Thus, they are intended to impart centers of weakness in the cured compositions in accordance with the invention. Upon the application of localized physical stress to the cured materials, such as by working with dental hand pieces or low-torque mechanical devices, these relatively weak polymer particles provide sources of defect in the cured articles allowing the same to fracture easily, to be cut and comminuted, or otherwise to be easily dissected and removed.

The frangibility enhancing materials are included in an amount sufficient to improve or impart frangibility to the cured compositions of the invention. In general, they are included in amounts up to about 20% by weight of the composition. It is preferred to include them in amounts of from about 5% to about 15% by weight of the composition. While this proportion also depends upon the identity of the frangibility enhancing material, for particulate polyalkylenes, amounts from about 8% to about 12% are most preferred.

After they are cured by irradiation with actinic light, especially visible light, the compositions of the present invention are coherent but frangible. By this it is meant that the compositions, such as in the form of polymerized masses or shaped bodies are capable of retaining their shape, and of serving the purposes for which they are designed such as dental and endodontic uses. At the same time, they are easily cut, dissected and removed as desired.

Frangibility is a qualitative term. As such, it has been described in extenso in the present specification. This description is believed to be adequate to teach persons of ordinary skill in the art what frangibility is in the context of the present invention. While it is entirely appropriate to describe the compositions of the present invention by what they do rather than by what they are, that is, by referring to the cured compositions as being frangible within the present context, and while the same is easily understood by persons having ordinary skill in the dental arts, at least one quantitative measure may be employed in estimating the degree of frangibility of a cured composition in accordance with the present invention.

Thus, an evaluation of the tensile strength of the compositions which have been cured provides a useful indication of the frangibility of such cured materials. In determining the tensile strength of a cured composition of the invention, it is preferred to employ a test method adopted by the American National Standards Institute/American Dental Association. The ANSI/ADA method which has been found to be most convenient for the present purposes is method 4.3.7 of ADA Specification Number 27 for Direct Filling Resins which determines 24 hour diametral tensile strength. Persons of ordinary skill in the art will appreciate that the foregoing tests will result in a range of values and that different forms of material may necessitate modification of the tests. Thus, it is emphasized that testing protocols and the values for tensile strength resulting from them are but an approximation which is useful in the evaluation of frangibility. Frangibility is best determined by the qualitative properties of the cured materials as described hereinbefore.

With the foregoing proviso, materials in accordance with the present invention generally exhibit measurable 24 hour diametral tensile strengths after curing of less than about 4,000 psi. It is more preferred that the materials exhibit such tensile strengths after curing of less than about 3,000 psi and even more preferred that such tensile strengths less than about 2,500 psi be exhibited. These relatively low 24 hour diametral tensile strengths are exhibited even while the cured compositions of the invention in the form of shaped bodies or masses retain their coherency as discussed above.

While the diametral tensile strength of the cured composition is believed to be the best quantitative measure of frangibility, other parameters are believed to be useful for estimating coherency along with frangibility as presently contemplated. Thus compressive strength may be a useful factor with values above about 1500 psi being preferred. Similarly, compressive modulus values above about 10,000 psi are preferred.

In accordance with the present invention, methods for forming coherent, but frangible, shaped bodies and masses are provided. These methods comprise providing an actinic light curable composition in accordance with the invention, forming the composition into a shape, and irradiating the shaped composition with actinic light for a time sufficient to cure the composition, thus providing the shaped body. The present methods are amenable to a wide variety of dental, endodontic, medical and industrial uses. The use for the "temporary filling" of excavated carious lesions and other tooth fillings together with the removable stopping of prepared endodontic spaces has been discussed hereinabove. Thus, a preferred method in accordance with the invention comprises treating a tooth by placing an actinic light curable composition into a prepared space in the tooth and irradiating the composition for a time sufficient to cure the composition to form a coherent but frangible mass. In accordance with a preferred embodiment relating to tooth treatment, the actinic light curable composition comprises a major proportion of inorganic filler, along with polymerizable resin, and frangibility enhancing material as discussed hereinabove. In accordance with another preferred embodiment, the placing and irradiating steps for treatment of a tooth are followed by a removal of the mass from the prepared space.

While present interest is centered around the dental arts, it is anticipated that industrial utility will be shown by the compositions and methods of the present invention. Thus, numerous applications wherein coherency, but frangibility, of polymerized masses and shaped bodies is desired may well benefit from the present invention. One likely candidate for such utility is the jeweler's art. Materials in accordance with the present invention are likely to show utility for replacing plaster, sculptured materials, waxes and the like for the preparation of, for example, cast items.

It is anticipated that the present materials and methods will be found to be quite flexible as to utility such that a wide array of industrial, medical, artistic and other applications for them will be found. The present invention is intended to contemplate such further developments.

The following examples are intended as illustrative only and are not to be construed as limiting.

EXAMPLE 1

A resin blend was prepared by mixing together the following components for one hour with a cage stirrer. The material is stored in a cold room and protected from light:

| | |
|---|---|
| The 1:1 reaction product of hydroxypropyl-methacrylate and 2,2,3-trimethylhexamethylene-diisocyanate (urethane acrylic resin) | 19.79% |
| The 1:1 reaction product of polypropylene glycol and isocyanatoethyl methacrylate (urethane polyether resin) | 79.16 |
| Camphoroquinone | 0.25 |
| Ethyl 4-dimethylaminobenzoate (recrystallized) | 0.80 |
| | 100.00% |

A visible light curable composition was prepared by mixing together the following components:

| | |
|---|---|
| Resin blend (as above) | 19.80% |
| Barium boron aluminum silicate glass (Corning 7724) | 54.46 |
| Spherical particulate polyethylene (Microthene TM FA 750-00) | 9.90 |
| Particulate fused quartz (RVH-9-95-3) | 9.90 |
| Gamma methacryloxypropyl trimethoxysilane-coated aluminum oxide (Meller) | 0.99 |
| Hydroxylated silicon dioxide (Hy-Sil EP TM) | 4.95 |
| | 100.00% |

All of the materials save for the resin blend are thoroughly tumbled together. Three-quarters of the blended powders are added to the resin blend and slowly mixed for five minutes in a Ross mixer. The mix is warmed to 40°–45° C. and mixed for a further ten minutes. The balance of the powder is added incrementally and mixing continued for one hour. The pressure is reduced to 120 mm of mercury and mixing is continued for a final thirty minutes.

This material exhibits good workability and is amenable to direct placement in prepared tooth spaces. Upon irradiation with a PRISMA LITE$^R$ visible light source, a product of Dentsply International, the material cures to a depth of about 4mm after about 10 seconds' irradiation resulting in a coherent mass of cured material interfacing tightly with the edges of the prepared space. The cured material is particularly suitable for temporarily filling of the outward portion of an endodontic space.

Ordinary dental hand cutting instruments and rotary burrs can be used to remove the cured composition from the prepared space. The material comminutes and is easily dissected, falling away clearly from the cavity margins without excessive effort.

EXAMPLE 2

A second visible light curable composition was prepared in accordance with the procedure of Example 1 except that the amounts of the urethane acrylic and urethane polyether resins were 79.16% and 19.79% respectively, that is, the proportions were reversed.

This material can be worked, placed and cured in a similar way to the material of Example 1. The resulting, cured, compositional mass is somewhat harder and stronger but less frangible, than the cured material of Example 1. While it may be removed from tooth spaces with hand instruments, it is preferred to use conventional burrs for this task. The material comes away cleanly from the wall margins and is easily removed without further trauma of the tooth.

EXAMPLE 3

The materials of Examples 1 and 2 were compared with two existing, commercial dental materials used for temporary and endodontic fillings. CAVIT ™, a product of the ESPE Company, is believed to comprise a polyvinyl acetate-based resin system while IRM$^R$, a product of the Caulk Division of Dentsply International Inc., is based upon zinc oxide and eugenol. The materials are also compared to PRISMA-FIL$^R$ visible light curable (permanent) restorative, a product of the Caulk division of Dentsply International Inc. The tests were conducted as follows:

Twenty-four hour diametral tensile by ANSI/ADA specification #30 for direct filling resins.

Twenty-four hour compressive strength by ANSI modified ADA specification #30 section 4.3.4.

Twenty-four hour compressive modulus as defined by ASTM D695, Section 11.4 and restorative dental materials, 5th Ed. by Craig R.G., and Peyton P.A., P. 63—Modulus of Elasticity.

Twenty-four hour tranverse strength by ISO 4049—1978 for dental resin based restorative materials.

Twenty-four hour flexural modulus by ISO 4049—1978 for dental resin--based restorative materials.

One week water sorption by ANSI/ADA specification #27 for direct filling resins.

One week water solubility by ANSI/ADA specification #30 for dental zinc oxide—eugenol type restorative materials.

Depth of cures—curing in a 11 mm thick Teflon mold, 5 mm ID. with ends covered by a sheet of Mylar. The open end is exposed to the curing unit, in this case, a Caulk Prismetics Lite ™, for the prescribed amount of time. After the proper exposure, the cured plug is pressed out and successive layers of uncured material is removed using 380 grit sandpaper. The bottom reading is taken using a Barber Colman impressor model GYZJ 935—medium. When the proper number is reached, the thickness of the specimen is measured in mm using a digital micrometer. The value is reported to the nearest 0.1 mm.

Barcol hardness—using the Barber Colman impressor, model GYZJ 935 medium, a reading is taken on a cured chip of material prepared as in ANSI/ADA specification #27, section 4.3.5 at 1 hour.

Shore hardness - using the Shore Durometer hardness type of instrument as described in ASTM D676, the material was placed in a small plastic right cylinder with dimensions 8 mm high and 10 mm in diameter, leveled off and then the Shore hardness indentor lowered into the material. This is repeated until the value on the Shore A hardness scale goes above 50. The time is then recorded when the reading reaches at least 50.

Microleakage—Microleakage test specimens consisted of box-type cavities prepared on the occlusal surface of extracted human molar teeth using a No. 58 carbide bur. Each cavity was designed so that it opened into the pulp chamber. Each cavity was rinsed with water and dried with compressed air. A water-moistened cotton pellett was placed at the bottom of the cavity to cover the pulp chamber. The respective filling material was placed in the cavity and pressed in with hand pressure. Each material was handled as described by the manufacturer. Specimens were stored 24 hours in distilled water at 37° C. then thermocycled in water baths between 10° C. and 50° C. for 540 cycles for one minute in each bath. Non-test areas were covered with nail polish and modeling compound before staining in a 50% aqueous silver nitrate solution. Leakage pattering were then developed under a photoflood bulb (GE-EBV) at a distance of 12 inches after the teeth were sectioned longitudinally using a diamond wheel. The leakage was evaluated by looking at the penetration along the filling material/tooth interface. The grading for this series was subjective. The worst leakage was judged to be full penetration into the pulp chamber. This was graded poor. Excellent was considered to be minimal leakage. Good was leakage less than ¼ the distance to the dentin/enamel junction. Medium would be greater than ¼ the distance to the junction, but not beyond it.

|  | Example 1 SOFT | Example 2 HARD | IRM ® | CAVIT ™ | PRISMAFIL ® |
|---|---|---|---|---|---|
| 24 Hr. Diametral Tensile Strength (PSI) | 522 | 1737 | 1500 | — | 7000 |
| 24 Hr. Comprehensive Strength (PSI) | 2,500 | 10,500 | 10,000 | 249 | 45,015 |
| Compressive Modulus (PSI/in) | 44,487 | 129,586 | 465,189 | 9,000 | 500,000 |
| Transverse Strength (PSI) | 830 | 2,500 | 1,350 | — | 7,200 |
| Flexural Modulus (PSI) | 18,355 | 288,150 | 99,825 | — | 671,567 |
| Depth of Cure (mm) |  |  |  |  |  |
| 5" | 6 | 3 | — | — | 2.1 |
| 10" | 11 | 6 |  |  | 3.8 |
| 20" | 16 | 7 |  |  | 5.0 |
| 1 Week Water Sorption, % Change in Weight | 6.0 | 2.3 | 0.45 | 15.3 | 0.8 |
| 1 Week, % By Weight Dissolved | ≦0.5% | 0.38 | 0.06 | 3.5 | ≦0.2 |
| Barcol Medium Hardness | 0 | 60 | 40 at 14 min. | 90 at 24 hrs. | 90 |
| Shore A 50 Hardness | 5 sec. | 5 sec. | 8 min. | 90 min. | 5 sec. |
| Microleakage | Good | Medium | Poor | Poor | — |

What is claimed is:

1. An actinic light curable composition, frangible when cured, comprising:
   a major proportion of inert filler, and
   polymerizable resin blend comprising:
      from about 15% to about 85% by weight of the blend of urethane acrylic resin;
      from about 15% to about 85% by weight of the blend of urethane polyether resin; and
      a photosensitizing system capable of curing the composition upon irradiation with actinic light; and
      from about 5% to about 15% by weight of the composition of a frangibility enhancing material comprising particulate organic polymer.

2. The composition of claim 1 curable to a coherent mass having a diametral tensile strength less than about 2,500 psi.

3. The composition of claim 1 wherein the urethane acrylic resin comprises the reaction product of a hydroxyalkyl acrylate or methacrylate with alkyl diisocyanate.

4. The composition of claim 1 where in the urethane polyether resin comprises the reaction product of polyether polyol and isocyanatoalkyl ester of alpha-beta unsaturated carboxylic acid.

5. The composition of claim 3 wherein the urethane polyether resin comprises the reaction product of polyether polyol and isocyanatoalkyl ester of alpha-beta unsaturated carboxylic acid.

6. The composition of claim 1 wherein the frangibility enhancing organic polymer comprises polyalkylene.

7. The composition of claim 5 wherein the frangibility enhancing material comprises particulate polyalkylene.

8. The composition of claim 1 wherein the photosensitizing system comprises an alpha diketone and an amine reducing agent and the actinic light is visible light.

9. The composition of claim 5 wherein the photosensitizing system comprises an a alpha diketone and an amine reducing agent and the actinic light is visible light.

10. The composition of claim 7 wherein the photosensitizing system comprises an alpha diketone and an amine reducing agent and the actinic light is visible light.

11. An actinic light curable composition, frangible when cured, comprising:
    actinic light polymerizable acrylic oligomer or oligomer blend;
    a major proportion of inert filler;
    a photosensitizing system capable of curing the composition upon irradiation with actinic light; and
    organic particulate polymer in an amount sufficient to render the cured composition frangible.

12. The composition of claim 11 wherein the cured composition has a tensile strength less than about 2500 psi and a compressive modulus greater than about 10,000 psi.

13. The composition of claim 11 wherein the particulate organic polymer is present in an amount of from about 5% to about 15% by weight of the composition.

14. The composition of claim 11 wherein the oligomer or oligomer blend comprises urethane oligomer.

15. The composition of claim 11 wherein the inert filler is inorganic.

16. The composition of claim 11 wherein the particulate organic polymer is polyalkylene.

17. A method of forming a coherent, but frangible, shaped body comprising:
    providing an actinic light curable composition comprising:
       a major proportion of inert filler;
       polymerizable resin blend comprising:
          from about 15% to about 85% by weight of the blend of urethane acrylic resin;
          from about 15% to about 85% by weight of the blend of urethane polyether resin; and
          a photosensitizing system capable of curing the composition upon irradiation with actinic light; and
       from about 5% to about 15% by weight of the composition of a frangibility enhancing material comprising particulate organic polymer:
    forming said composition into a shape; and
    irradiating the shaped composition with actinic light for a time sufficient to cure the composition to provide the shaped body.

18. The method of claim 17 wherein the shaped body has a diametral tensile strength less than about 2,500 psi.

19. The method of claim 17 wherein the urethane acrylic resin comprises the reaction product of a hydroxyalkyl acrylate or methacrylate with alkyl diisocyanate.

20. The method of claim 17 wherein the urethane polyether resin comprises the reaction product of polyether polyol and isocyanatoalkyl ester of alpha-beta unsaturated carboxylic acid.

21. The method of claim 19 wherein the urethane polyether resin comprises the reaction product of polyether polyol and isocyanatoalkyl ester of alpha-beta unsaturated carboxylic acid.

22. The method of claim 17 wherein the frangibility enhancing organic polymer comprises polyalkylene.

23. The method of claim 21 wherein the particulate organic polymer comprises particulate polyalkylene.

24. The method of claim 17 wherein the photosensitizing system comprises an alpha diketone and an amine reducing agent and the actinic light is visible light.

25. The method of claim 23 wherein the photosensitizing system comprises an alpha diketone and an amine reducing agent and the actinic light is visible light.

26. In an actinic light curable composition comprising ethylenically unsaturated, polymerizable resin or resin blend, inert filler and a photosensitizing system,
    the improvement comprising including in the composition particulate organic polymer in an amount sufficient to render the cured composition frangible.

27. The composition of claim 26 wherein the particulate organic polymer comprises polyalkylene.

* * * * *